United States Patent [19]

Roth

[11] 4,282,317

[45] Aug. 4, 1981

[54] PECTIN CULTURE MEDIA AND METHOD

[76] Inventor: Jonathan N. Roth, 19676 Riverview Dr., Goshen, Ind. 46526

[21] Appl. No.: 6,253

[22] Filed: Feb. 21, 1979

Related U.S. Application Data

[63] Continuation-in-part of Ser. No. 3,258, Jan. 15, 1979, abandoned, which is a continuation-in-part of Ser. No. 970,347, Dec. 18, 1978, Pat. No. 4,241,187.

[51] Int. Cl.$^3$ .................. C12Q 1/04; C12N 5/00; C12N 1/20
[52] U.S. Cl. .................. 435/34; 435/240; 435/253; 106/205; 106/208
[58] Field of Search ............. 435/253, 34, 240; 536/2; 106/205, 208

[56] References Cited

U.S. PATENT DOCUMENTS

| | | | |
|---|---|---|---|
| 2,358,430 | 9/1944 | Willaman et al. | 536/2 |
| 2,540,050 | 1/1951 | Leo et al. | 536/2 |
| 2,701,767 | 2/1955 | Twieg et al. | 536/2 |
| 2,970,948 | 2/1961 | Stevens | 435/253 |
| 3,814,670 | 1/1974 | Freake et al. | 435/253 |
| 3,846,241 | 11/1974 | Faur et al. | 435/253 |
| 3,935,067 | 1/1976 | Thayer | 435/253 |
| 4,016,351 | 4/1977 | Eschinasi | 536/2 |

OTHER PUBLICATIONS

Chem. Abst. 85:139,679b.
Levin et al., *A Compilation of Culture Media*, pp. 78 & 79, 1930.

*Primary Examiner*—Allan Lieberman
*Attorney, Agent, or Firm*—Donald A. Kaul

[57] ABSTRACT

A method for preparing a gelled biological growth medium which comprises combining a liquid growth medium and low methoxyl pectin material to a culture-growth container having a growth-compatible gel including a multivalent metal cation material therein, the pectin material being the sole or essentially the sole functional gelling agent of the growth medium gel.

34 Claims, 4 Drawing Figures

PECTIN CULTURE MEDIA AND METHOD

REFERENCE TO RELATED APPLICATIONS

This application is a continuation-in-part of my earlier, co-pending application, Ser. No. 3,258, filed Jan. 15, 1979, now abandoned, which is a continuation-in-part of my earlier, co-pending application, Ser. No. 970,347, filed Dec. 18, 1978, now U.S. Pat. No. 4,241,187.

BACKGROUND OF THE INVENTION

1. Field of the Invention

The present invention relates to the field of culture media and methods for producing the same, and more particularly to culture media including pectin as the gelling agent.

2. Description of the Prior Art

A considerable variety and number of culture media are disclosed in the prior art. A corresponding number of methods for producing such media are also known. In general, media used for the growth of living cells, tissues or organisms contain certain ingredients. These ingredients include water, nutrients (generally a carbon source, a nitrogen source, and smaller amounts of other essential elements), buffers, and often a gelling or solidifying agent.

The majority of the biological media present in the prior art utilize agar, gelatin or silica gel as solidifying agents, also referred to herein as gelling agents. Disadvantages are associated with each of these materials as solidifying agents. Agar is obtained from marine algae which must be harvested from naturally occurring populations. The supply of agar correspondingly fluctuates from year to year, while the demand for solidifying agent continues to grow. The price for agar has steadily increased as a result, and the present price is relatively high. Another problem associated with the use of agar is the need to dispense the agar into its container while quite warm, since the agar solution may solidify at about 40°–45° C. A temperature of 45° is too high for some cells to withstand without adverse effects.

Gelatin is easily obtained at a relatively reasonable cost, but it is easily hydrolyzed by many micro-organisms, which causes the gel to become a liquid. This is undesirable except in those cases where the hydrolysis is being used as a diagnostic biochemical test. Further, gelatin is generally available as a nutrient source for the organisms in contact with it, and as a result may interfere with the testing of specific nutrient sources. Gelatin also has the undesirable property of liquifying at quite low temperatures, so that media incorporating it as a gelling agent cannot be incubated above 25° C. with assurance that the medium will retain its solid consistency. Disadvantages associated with silica gel include the relatively high cost of silica gel, and the complicated procedure required to prepare a medium using silica gel.

Pectins are routinely used as the thickening or gelling agent in the production of jams and jellies. However, the process generally used involves high sugar concentrations and low pH, neither of which is suitable for general microbial or tissue culture work. In fact, the high sugar and low pH characteristics are useful factors in preventing the establishment of growing, contaminating organisms in the jelly products.

Referring specifically to the prior art, there is disclosed in U.S. Pat. No. 2,970,948, issued to Stevens on Feb. 7, 1961, a culture medium in which pectin may be used. According to the procedure of the Stevens patent, a citrus serum agar culture is prepared by the following steps:

(1) adding pectinesterase to remove pectin by precipitation from fruit juice;
(2) concentrating the fruit juice serum;
(3) mixing with the fruit juice serum certain dry ingredients; and
(4) drying the resulting mixture under a vacuum.

The Stevens patent discloses that included in the dry ingredients must be a gelling agent, which may include agar, gelatin or water soluble salts of pectic acid or alginic acid. It is further indicated that the gelling agent, which may include the pectic acid salts, is to be one which is capable of setting to a gel at room temperature upon cooling an aqueous solution thereof. In contrast to the method and media of the Stevens patent, the present invention involves the combination of a specified type of pectin and cations, particularly to produce a gel having pectin as the sole or essentially sole functional gelling agent.

In U.S. Pat. No. 2,373,729, issued to Willaman on Apr. 17, 1945, there is disclosed a thickening agent comprising a dry, powdered mixture of pectin, pectase and a water-soluble salt of a polyvalent metal. It is disclosed that the thickening agent is useful in the preparation of jellies, puddings, syrups and catsup, as well as non-food materials. The thickening agent is used by combining the dry-powdered mixture with an aqueous solution under certain conditions of temperature and pH. A different method for making a pectic preparation is disclosed in U.S. Pat. No. 2,540,050, issued to Leo and Taylor on Jan. 30, 1951. A gelatinous pectin/aluminum hydroxide co-precipitate is obtained from a pectin extract of fruit or vegetable material. The co-precipitate is then treated with pectase to provide the pectic material indicated to be useful in preparing jellies. In U.S. Pat. No. 3,360,440, issued to Haab et al., there is disclosed a cold water reconstitutable microbiological medium utilizing a modified cellulose as the sole gelling agent. U.S. Pat. No. 3,935,067, issued to Thayer on Jan. 27, 1976, discloses a culture media comprising inorganic water-swellable support material or water-absorbing clay mineral as a substitute for agar as a growth support and culture media.

A slow-set pectin is disclosed in U.S. Pat. No. 3,835,111, issued to Ehrlich and Cox on Sept. 10, 1974. The pectin material is prepared by contacting pectin with an ammoniacal alcohol solution at low temperature. The resulting pectin has reduced sensitivity to alkaline earth metal ions, which is indicated in the Ehrlich patent as producing a pectin suitable for preparation of sugar jellies. The pectin of the Ehrlich patent has a degree of methoxylation of 60–70%. A low methoxyl pectin is disclosed in U.S. Pat. No. 3,622,559, issued to Wiles and Smit on Nov. 23, 1971.

In U.S. Pat. No. 3,197,384, issued to Goldman on July 27, 1965, there is disclosed a process for determining the microbial sensitivity to certain anti-microbial agents. In the method of the Goldman patent, the anti-microbial agent is impregnated at premarked areas on a filter pad or sheet of filter paper. The pad or paper is then wetted with an inoculated broth and the reaction of the bacteria in the broth to the anti-microbial agent is perceivable over time.

SUMMARY OF THE INVENTION

Figure 1:
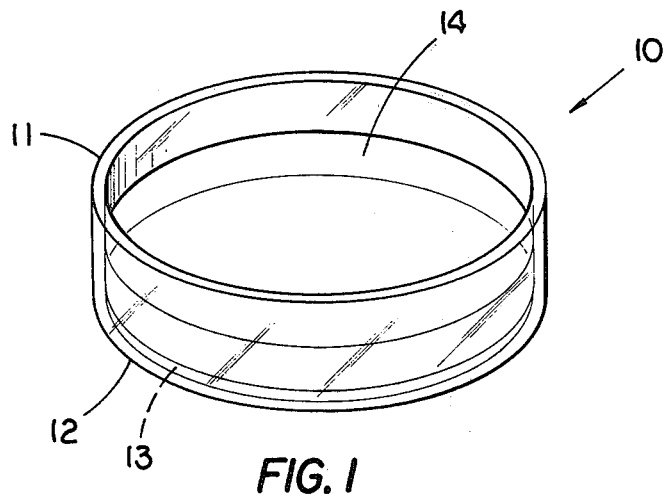
FIG. 1 is a perspective view of one embodiment of the present invention.
Figure 2:
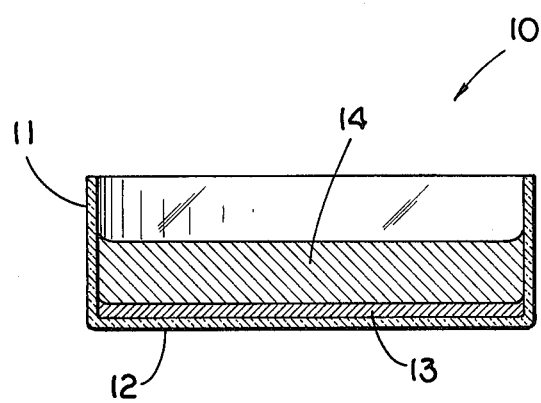
FIG. 2 is a side, elevational view of the embodiment of FIG. 1.
Figure 3:
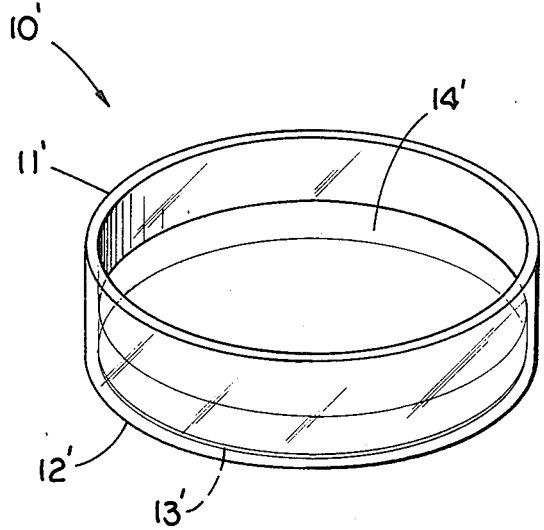
FIG. 3 is a perspective view of an alternate embodiment of the present invention.
Figure 4:
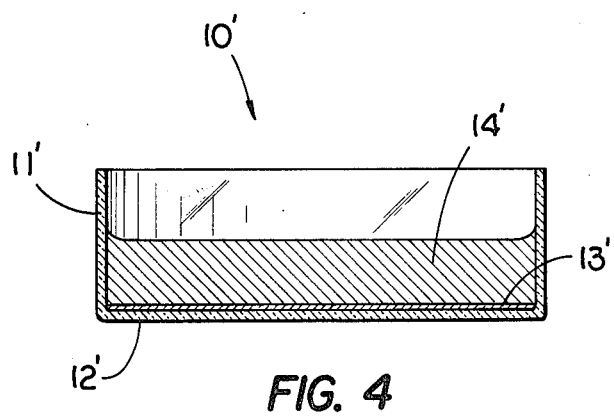
FIG. 4 is a side, elevational view of the embodiment of FIG. 3.

The present invention involves the preparation of a gelled biological growth medium having pectin as the gelling agent. The method involves the combination of a liquid growth medium and a low methoxyl pectin material with a growth-compatible gel containing a suitable amount and type of metal cation material to produce gelling of the liquid growth medium. In a preferred embodiment, an agar gel containing calcium chloride is provided in a container, such as a Petri dish, and an aqueous mixture of the liquid growth medium and pectin is poured into the container, whereby gelling of the medium subsequently occurs. The present invention further comprises the combination of a culture-growth container and a growth-compatible gel containing a multivalent metal cation material.

It is an object of the present invention to provide a method for preparing a gelled biological growth medium which may be simply and quickly performed.

It is a further object of the present invention to provide a method for preparing a gelled biological growth medium which utilizes relatively inexpensive and readily available materials.

Another object of the present invention is to provide a method for preparing a gelled biological growth medium which does not require the growth medium to be subjected to elevated temperatures.

A further object of the present invention is to provide a method for preparing a gelled biological growth medium utilizing pectin as the sole or essentially sole gelling agent, which pectin will not materially interfere with tests using the medium, and which may contribute to the variety of tests which can be used with the growth medium.

It is another object of the present invention to provide a method for preparing a gelled biological growth medium which utilizes materials which may be readily and conveniently packaged in kit form.

It is a further object of the present invention to provide a gelled biological medium, and method for producing same, in which pectin is the sole or essentially sole solidifying agent.

Another object of the present invention is to provide a combination useful in the preparation of a gelled biological growth medium.

Additional objects and advantages of the present invention will become apparent from the description which follows.

DESCRIPTION OF THE PREFERRED EMBODIMENT

Disclosed in the prior art is a variety of culture media and methods for producing the same. The culture media produced in accordance with the teachings of the prior art are well suited generally to the various applications of such media, but certain disadvantages may be associated with these media or methods. The present invention provides a simple and expedient method for preparing a gelled biological growth medium. Moreover, the method described herein utilizes relatively inexpensive and readily available materials and avoids disadvantages associated with the prior art.

In accordance with the present invention, a liquid culture growth medium is prepared which includes a pectin material as the gelling agent. The present invention utilizes a low methoxyl pectin which is defined for the purposes herein as having from about one percent to about eight percent methoxyl content. Stated in other terms, the low methoxyl pectin has a degree of methoxylation of about seven to about fifty percent, the degree of methoxylation referring to the extent of esterification of the carboxyl groups with methoxyl groups. In a preferred embodiment of the present invention the low methoxyl pectin has between about three and about seven, and most preferably approximately a five percent methoxyl content, or a degree of methoxylation of from about twenty-five to about forty percent.

The pectin should be present in the growth medium in an amount effective to provide sufficient gelling of the growth medium upon combination of the growth medium with a suitable metal cation material. The amount of pectin will vary with the degree of methoxylation, and also upon other factors such as the extent of gelling desired. However, the amount of pectin desired may be readily determined by simple and direct experimentation. It has been determined that most preferably the pectin, particularly with an approximately five percent degree of methoxylation, is present in an amount of from about ten to about thirty gram of pectin per liter of growth medium.

The liquid growth medium containing the low methoxyl pectin may include a variety of other constituents. In general, the medium may correspond to the wide variety of growth media used in the prior art for microbial and/or tissue cultures, except to the extent that components which would break down or interfere with the pectin should generally not be included. Typically, the culture medium would include several other constituents including 2-10 grams/liter of a carbon source, such as glucose or other sugars, 2-10 grams/liter of nitrogen, and other micronutrients in the form of natural products (e.g. tryptone, peptone, beef extract, yeast extract, etc.) or synthetic materials (potassium nitrate and various other microelements). The exact nutrients and concentrations which are useful in the liquid growth medium employed in the present invention are innumerable, and as always in the preparation of a growth medium would be selected according to the particular situation.

The limitations for the other constituents of the medium prepared in accordance with the present invention are generally the same as exist for any other culture media. Typical ranges for certain media components have already been stated. In another aspect, the sugar concentration of the growth medium of the present invention would generally be less than about ten percent, and the pH would preferably range from 3.5 to 8, primarily from about 6 to about 7. In contrast, food products such as jellies or jams typically include more than fifty percent and perhaps eighty percent sugar as the percent of total solids in the product.

The biological growth medium produced in accordance with the present invention would also preferably include one or more buffers to control the pH of the media. The buffers must be non-toxic to micro-organisms and must not degrade the pectin to a point of uselessness. Generally, buffers containing the elements potassium or sodium in combination with phosphate or carbonate groups are non-toxic in minor amounts. Any buffers may cause breakdown or complexing with pectins, and therefore the best results are obtained if the growth medium and the buffers are separately sterilized and then combined after cooling. The variety of buffers which would be useful with the pectin-containing medium include the following: $NaH_2PO_4$, $Na_2HPO_4$, $Na_3PO_4$, $NaHCO_3$ and $Na_2CO_3$, with the tribasic sodium phosphate ($Na_3PO_4$) being found to be particularly suitable. Other useful buffers include citric acid and sodium citrate; acetic acid and sodium acetate, citric acid and dibasic sodium phosphate, succinic acid and sodium hydroxide; monobasic sodium or potassium phosphate and dibasic sodium or potassium phosphate; and tris-maleate. The suitability of other buffers or buffer systems are readily predictable and/or determinable by direct and simple experimentation.

In accordance with this invention, an acceptable, solid gel is obtained at a pH of as high as about 9. The prior art literature suggests that pectin as a gelling agent requires an acid pH, typically below about 4. It was therefore an unexpected result that a culture medium useful at pH as high as about 9 could be obtained using pectin as the gelling agent.

The pectin-containing growth medium is combined with a multivalent metal cation material suitable to produce gelling of the growth medium. It is known that low methoxyl pectin is sensitive to the presence of various multivalent cations such as calcium, and will form gels when combined with such cations. As is well known, the various multivalent metal cations may be provided most readily as the metal salts, most preferably those which are water soluble. As in the case of the pectin included in the growth medium, a sufficient amount of metal cations must be provided to produce the desired gelling of the growth media.

In general, the relative amounts of pectin and metal cations to produce adequate gelling are known and understood in the art, and additionally the amounts desired for use in the present invention may be readily determined by direct experimentation. Sufficient amount of cation is required to produce a good, firm gel formation, but not so much that the gel is hard, brittle or tends to syneresis (weeping). The amounts of the pectin-containing growth medium and/or metal cation material are typically and preferably predetermined to provide the proper gelling, particularly in preparing the materials in a kit form. In a preferred embodiment of the present invention, the cation concentration is from about 15 to about 30 milligrams of calcium cations per gram of pectin. Equivalent amounts of other multivalent metal cations could equally be used. In any event, the amount of cation most preferred will depend on the degree of methoxylation and the amount of the pectin.

The present invention 10 contemplates the combination of the growth medium and metal cations within a culture-growth container. A suitable culture growth container 11, such as a test tube or Petri dish is provided, such container being defined as one which is appropriate and used for containing the medium during culture growth. Typically, the culture growth container is one which permits or facilitates observation or evaluation of the culture growth. A growth-compatible gel 13 containing the metal cation material is caused to form in the culture-growth container typically on the bottom 12 thereof, and the liquid growth medium and pectin material are added thereto. Contact of the medium with the growth-compatible gel will result in a diffusion of the cations through the pectin solution and the consequent formation of a growth-medium gel 14. As indicated, the concentration of the cations in the growth-compatible gel and/or the amount of the growth-compatible gel in the culture-growth container is determined to provide a suitable amount of the metal cations for gelling of the growth medium.

The growth-compatible gel may comprise a variety of gels presently known for use in connection with media for biological growth. As recited and described in the prior art, gels of this type may include, for example, gels utilizing agar, gelatin, silica gel, or carageenan as the solidifying or gelling agents. Other materials could also suitably be used as the carrier for the multivalent metal cations. Such carriers should be inert and nontoxic to living cells, and should not be hydrolized during the process. The growth-compatible gel caused to be formed in the culture-growth container is prepared and handled in the usual fashion. Although these growth-compatible gels may include growth nutrients and other non-toxic or non-interfering components, such as not required or preferred. The growth-compatible gel may simply and preferably does include only the constituents necessary to provide the gel, as well as the multivalent metal cation material as previously described.

It has been noted that the amount of multivalent cation material necessary will vary with a number of factors which need not be fully described since the factors are readily apparent and the determination may be readily accomplished by simple and direct experimental techniques. As indicated, a sufficient amount and type of multivalent cation material must be included to produce the desired gelling of the growth medium as a result of the presence of the low methoxyl pectin material. Understandably, the characteristics of the growth-compatible gel will to some extent control the amount of multivalent metal cation material necessary to provide sufficient interaction with the low methoxyl pectin material to produce the desired gel. Further, the configuration of the culture-growth container and of the growth-compatible gel contained therein will to some extent control the amount of multivalent metal cation material required to be present in the growth-compatible gel. For example, the ratio of the surface area of the growth-compatible gel to the volume of the growth-compatible gel will affect the amount of metal cation material required.

In a preferred embodiment of the present invention, the growth-compatible gel is located within a Petri dish, as a thin, generally uniform film layer coating the bottom of the dish. In this embodiment, a concentration of calcium chloride of about 2-5 grams per 100 milliliters of a 2% agar solution has been found to be most preferable, particularly when combined at a ratio of about one to ten with a liquid growth medium solution containing from about ten to about thirty grams of pectin per liter of medium.

The growth-compatible gel preferably would not include a pectin material as a substantial functional gelling agent. Thus, although minor amounts of a pectin material may be present, it is preferred that the substantial extent of the gelling affect is the result of other gelling agents. A reason for utilizing gelling agents other than the pectin in the growth-compatible gel is the relationship of the pectin material with the multivalent metal cation material for which the growth-compatible gel is a support and carrier. As previously indicated, an excess of the multivalent metal cation material can produce syneresis or weeping. The amount of the multivalent metal cation material which may suitably be provided in the growth-compatible gel is therefore limited in the instance of using pectin as the solidifying or gelling agent.

A net or mesh of natural or synthetic material may be used with the medium of the present invention as with prior art media. A net with a uniform mesh size, such as five millimeters, provides the function of allowing the observer to have measured fields outlined on the Petri dish or other container. A net or mesh also permits the observer to see completely through the solidified medium rather than limiting viewing from one side as would occur with an opaque, absorbent pad or paper.

It is a particular aspect of one embodiment of the present invention that the low methoxyl pectin material is utilized as the sole or essentially the sole, functional gelling agent. The term sole functional gelling agent is used herein as meaning the only constituent of the composition which has a significant function as a gelling agent. This would, for example, exclude agar or gelatin as significant functional gelling agents. However, just as minor traces of impurities would not necessarily interfere with or contribute to the functioning of the pectin material, minor amounts of agar or other gelling agents could be present and are contemplated in this particular embodiment, if not present in such quantities and forms as to significantly contribute to the gelling of the culture medium.

Applicant has identified the term low methoxyl pectin as referring to pectin having from about one to about eight percent methoxyl content, or from about seven to about fifty percent degree of methoxylation. It has further been indicated that the amount of metal cation required will depend upon the degree of methoxylation of the pectin material, as well as other factors. It has been determined that the lower the degree of methoxylation of the pectin material, the more sensitive the pectin becomes to contact with the metal cation. As a result, pectin having a very low degree of methoxylation, such as pectic acid which essentially has a zero percent methoxyl content, is too sensitive to be readily useful in the preparation of a gelled culture medium. The high sensitivity to metal cation causes a gel to immediately form in the vicinity of the cations upon contact, and lumps and uneven surfaces in the medium will typically result. The opposite effect resulting from a reduced sensitivity to metal cations occurs with pectin having a degree of methoxylation substantially above the range recited for the present invention.

In a particularly preferred method of the present invention, a gelled biological growth medium is prepared by combining predetermined amounts of a liquid growth medium and a low methoxyl pectin material with a predetermined amount of growth-compatible gel containing a multivalent metal cation material. These amounts are selected in accordance with the prior descriptions to provide a suitable gel formation. In this aspect of the invention, the low methoxyl pectin material is essentially the sole functional gelling agent, and suitably is the sole functional gelling agent.

As previously described, one or more of these components is preferably presterilized, and may conveniently be provided in a pre-packaged kit form. In such a kit form, the three components may be separately packaged and sterilized, or the liquid growth medium and low methoxyl pectin material may be mixed in predetermined proportions to later be combined with the growth-compatible gel. The liquid growth medium and low methoxyl pectin material, either separately or as a pre-mix, are then added to the culture growth container and gelling results upon contact of the low methoxyl pectin material with the multivalent metal cation material.

Other methods for providing the multivalent metal cation material in the culture-growth container are contemplated. As disclosed in my prior, co-pending patent applications previously identified, the metal cation material may be conveniently provided by impregnating a support material, such as a filter pad or paper, with a solution of the material, or by spraying the material directly onto the surface of the liquid growth medium/pectin material, or simply by mixing the components together prior to delivery to the culture-growth container. The present application presents the method by which the multivalent metal cation material is charged to the culture-growth container and supported therein. There has been described the procedure by which the multivalent metal cation material is located within a gel which is caused to form within the culture-growth container. Alternatively, a solution of the metal cation material may be directly applied to the culture-growth container and allowed or caused to dry to deposit the metal cation material upon the surface of the culture-growth container. For example, a solution of the multivalent metal cation material, with water or other solvents, may be sprayed, painted, or otherwise applied to the surface of the culture-growth container and permitted to dry thereon. Most desirably, the method of applying the solution would provide a uniform depositing of the metal cation material upon the surface.

Referring to the drawings, there is shown an embodiment of the present invention 10' in which a culture-growth container 11' is utilized. The multivalent metal cation material forms a thin film layer 13' on a surface of the container, such as the bottom 12' of container 11'. The growth-medium gel 14' solidifies thereover.

The present invention further provides a biological growth medium gel as produced in accordance with the methods of the present invention. The growth medium gel preferably comprises growth nutrients and as the essentially sole functional gelling agent a low methoxyl pectin material. The pectin material is suitably the sole functional gelling agent in the growth medium gel of the present invention. In this regard, the term gelling agent is understood as referring to the functioning of the pectin to form the gel and in the existence of the pectin material as the gel network or structure. The gel of the present invention may comprise various constituents in accordance with the earlier descriptions relating to methods of forming such a gel.

The biological growth medium gel suitably consists essentially of growth nutrients, buffers, water, and a low methoxyl pectin material as the essentially sole or sole functional gelling agent. The low methoxyl pectin material is preferably present in an amount of from about ten to about thirty grams of pectin per liter of medium.

In one aspect, the present invention provides the combination useful in the preparation of a gelled biological growth medium which comprises a culture-growth container and a growth-compatible gel located in the container. The growth-compatible gel is constituted as previously described, and in this particular embodiment includes a multivalent metal cation material in an amount of at least about 4 grams per 100 milliliters of the water/agar mix. Preferably the growth-compatible gel consists essentially of the multivalent metal cation material, agar and water. As previously indicated, the growth-compatible gel in this embodiment of the invention is prepared and caused to form within the culture-growth container in accordance with usual techniques. The combination of the culture-growth container and the growth-compatible gel containing a multivalent metal cation material may then be subsequently used to provide a gelled biological growth medium in accordance with the methods previously described. Briefly, a liquid growth medium and a low methoxyl pectin material are delivered to the culture-growth container, and upon contact with the growth-compatible gel will solidify.

An alternate embodiment of the present invention comprises the combination useful as a biological growth medium which includes a culture-growth container, a growth-compatible gel and a growth-medium gel. The growth-compatible gel is constituted as previously described, and forms a first layer in the container. The growth-medium gel forms a second layer adjacent to the growth-compatible gel in the container, and also is consituted as previously described. The growth-medium gel may comprise the components previously described with respect to the liquid medium, and further comprises a low methoxyl pectin material as essentially the sole functional gelling agent. Suitably the low methoxyl pectin material is the sole functional gelling agent for the growth-medium gel.

With respect to the growth-medium gel, the low methoxyl pectin material is preferably present in an amount from about ten to about thirty grams of pectin per liter of growth-medium. The growth-medium gel may further comprise one or more buffers selected from the group consisting of $Na_2HPO_4$, $NaH_2PO_4$, $Na_3PO_4$, $NaHCO_3$ and $Na_2CO_3$. It is further preferred that the low methoxyl pectin material have approximately a 5% methoxyl content, and that the multivalent metal cation material comprise calcium cations. Most preferably the calcium cations are present in an amount from about fifteen to about thirty milligrams of calcium cations per gram of pectin. It is preferred that the growth-compatible gel comprise an agar gel although the other gels as previously indicated may be utilized. Preferably, the volume of the growth-medium gel is from about three to about twenty times the volume of the growth-compatible gel, and in a particularly preferred embodiment there is combined about ten milliliters of growth-medium gel to about one milliliter of growth-compatible gel which may suitably be performed in a sixty millimeter diameter Petri dish.

The present invention introduces unique concepts and methodology into the area of preparing biological growth media, and specifically incorporates pectin into such media as the sole gelling or solidifying agent. The present invention provides a simple, straightforward method of utilizing pectin as the gelling agent. Particularly in the preferred method of the present invention, preparation of a biological growth medium utilizing pectin as the gelling agent is accomplished by the use of presterilized components not requiring the use of special sterilizing equipment such as an autoclave or oven.

For example, the liquid growth medium including pectin may be and preferably is presterilized and packaged, and the culture-growth container having the growth-compatible gel including the metal cation material therein is correspondingly presterilized and packaged. Also any or all of the materials (liquid growth medium, low methoxyl pectin material, growth-compatible gel, growth-medium gel and solution of metal cation material) may be and preferably are presterilized and packaged for later use. The preparation of a gelled growth medium in a culture growth container may therefore be easily accomplished without substantial time and without the use of other equipment. The present invention is therefore particularly suited for use in teaching laboratories or other environments where equipment is limited and the time and/or expertise of persons preparing a growth medium are also limited.

Additional advantages are also associated with the method of the present invention. In one aspect, the liquid growth medium including the low methoxyl pectin may be dispensed either hot, warm or chilled, with solidification occurring in any case upon combination in the culture-growth container. Temperature independence is a particularly notable advantage over the classical agar medium in techniques such as dilution plating for population determination or separation of a mixture of various microbial types. In the dilution technique, an aqueous mixture of the microbes is added to the ungelled medium, mixed for homogeneity, and then poured into Petri dishes and allowed to gel. If agar is used as the gelling agent for the growth-medium gel, the medium must be at a temperature of about 45° C. or higher when the microbes are added due to the fact that solidification will occur below that temperature. Such a high temperature will be harmful to many delicate microbes, and may actually kill or inactivate many, or cause undesirable changes such as mutation. This would be expected to result in an inaccurate picture of the original microbial mixture. Such problems are avoided by the present invention since the microbes can be mixed with the liquid growth medium at as cool a temperature as desired.

The usefulness of the biological growth medium produced in accordance with the present invention is evidenced by the lack of temperature dependence previously described, as well as the fact that most microorganisms are incapable of hydrolyzing the gelled pectin. The medium may also be used with Procaryotic organisms of the kingdom Protista, with Eucaryotic micro-organisms, or in cell or tissue culture techniques. The medium may also be used in demonstrating which microbes produce pectolytic enzymes, since such organisms may effect the hydrolysis of the media. In addition, the media produced by the procedures of the present invention are easily and accurately reproducible such that a continuing series of experiments or a duplication of an experiment can be performed with accuracy.

The procedures utilized in the present invention are very straightforward and well known to those skilled in the art. As a particular example of the method of the present invention, the following procedure is recited in detail. First, the pectin is blended with the nutrient broth solution at an amount of 20-25 grams per liter and in a manner to avoid the formation of insoluble lumps. The nutrient-pectin broth is then buffered with $Na_3PO_4$ to provide a pH in the range of 6-7. The nutrient-pectin broth is then sterilized in an autoclave at 10-15 pounds per 10-15 minutes. Alternatively the nutrient-pectin broth and the buffers may be sterilized separately and combined following sterilization. Or alternatively, the pectin may be dissolved in water at an amount of 20-25 grams/liter and in a manner to avoid the formation of insoluble lumps, while the nutrient and buffer may be combined separately and the two solutions unified following separate sterilization.

A solution containing 2% (2 grams per 100 milliliters deionized or distilled water) agar-agar and calcium chloride is prepared. Alternatively, other compounds including multivalent metal cations may be employed as is well known in the art relating to agents for use with pectin to provide a gel. Typically, the calcium compounds including chloride, nitrate or phosphate are particularly desirable, and the ideal agent would be water soluble. As previously indicated, the concentration of the calcium chloride or other multivalent metal cation material is determined to provide the proper metal cation concentration to cause solidification of the nutrient-pectin composition when poured over the solidified agar gel.

The solution of the 2% agar and metal cation material is prepared by suitable means, such as by dissolving the materials in water heated at 15 pound pressure and about 120° C. in an autoclave. The sterile agar mixture is then dispensed while hot into a Petri dish sufficiently to cover the bottom of the sterile dish. The mixture solidifies quickly forming a gel film adhering to the inside of the Petri dish base. Alternatively, the agar mixture may be dispensed into non-sterile Petri dishes or containers and, after solidification, they may be sterilized in customary fashions such as by ethylene oxide gas or radiation.

The nutrient-pectin broth, or liquid growth medium, is preferably presterilized, and then is dispensed into the dishes or other culture-growth container on top of the agar, growth-compatible gel film. The presence of the multivalent metal cations causes the liquid growth medium to solidify generally in about 2-4 hours. The solidified growth-medium is then inoculated with microorganisms, and is incubated either right side up or upside down.

The present invention is useful with a variety of culture-growth containers. The invention is particularly well-suited to use with disposable containers. Preferably the volume of the growth-medium gel is about three to about twenty times the volume of the growth-compatible gel. In the instance of use with Petri dishes and other containers, a suitable combination has been found to be about one milliliter of growth-compatible gel to about ten milliliters of growth medium gel in a sixty milliliter Petri dish.

The following examples further exemplify biological media prepared in accordance with the present invention.

EXAMPLE I

A general microbiological medium for the growth of bacteria, molds and yeast was formulated as follows.

| | |
|---|---|
| Tryptone | 2 gm |
| Peptone | 2 gm |
| Yeast extract | 2 gm |
| Glucose | 2 gm |
| LM Pectin | 25 gm |
| Deionized water | 1 liter |

This formulation is sterilized by autoclaving and following the autoclaving and cooling of the medium, a combination of $Na_3PO_4$ and $Na_2CO_3$ (presterilized) is added to adjust the pH of the medium.

Numerous bacteria, yeast, and molds have been grown successfully on this formulation.

EXAMPLE II

A specific differential medium known as Eosin Methylene blue agar is used to identify the presence of *Escherichia coli* from other similar bacteria. *E. coli* grows with a green sheen on this medium in comparison to *Enterobacter aerogenes* which grows as a gummy pink culture.

The following medium was prepared which, in preliminary tests, worked very well in differentiating these 2 organisms.

| | |
|---|---|
| Peptone | 5 gm |
| Lactose | 5 gm |
| Eosin y | 0.4 gm |
| Methylene blue | 0.065 gm |
| LM Pectin | 25 gm |
| Deionized water | 1 liter |

The above formulation was sterilized and then adjusted to a pH of 7.1 with $Na_3PO_4$ and $Na_2CO_3$ (presteril).

EXAMPLE III

As previously indicated, the above media of Examples I and II were utilized in preparing a gelled biological growth media in accordance with the present invention. Initially, an agar mixture prepared as previously described was delivered to a Petri dish and allowed to cool and therefore solidify. The formulations of Examples I and II were then added to different Petri dishes containing the solidified agar mixture. This procedure is followed using the different proportions of the formulations with the agar gel ranging from about three to about twenty times the volume of each formulation to the volume of the agar gel. Excellent results are obtained.

EXAMPLE IV

The procedures of Example III are followed except that instead of the agar mixture, other standard gel formulations were utilized to provide the growth-compatible gel. The other growth-compatible gels included gelatin, carageenan and silica gel as the solidifying or gelling agents. The addition of the formulations of Examples I and II produced excellent growth-medium gels.

EXAMPLE V

The procedures of Example III are repeated except that instead of utilizing an agar gel as a carrier for the calcium chloride, a solution of the calcium chloride was applied directly to Petri dishes. The solutions were variously applied by spraying with an atomizer and by painting the solution directly onto the dishes. Upon combination with the formulations of Examples I and II, suitable gels were produced. These procedures are performed utilizing an aqueous solution of calcium chloride, and also a mixture comprising 5-10 grams of methyl cellulose and about 4 grams of calcium chloride to 100 milliliters of water, and similar results were obtained.

As further examples of the methods and medium gel of the present invention, variations of the above examples are conducted. Performing the methods of the above examples utilizing alternatively a low methoxyl pectin material having about one, three, five and eight percent methoxyl content provides in each instance a suitable culture medium gel. Practicing the methods of the prior examples similarly produces a suitable gel when the liquid growth medium and low methoxyl pectin material are either separate or in combination, and the method also suitably comprises the addition of the liquid growth medium and the multivalent metal cation prior to addition of the low methoxyl pectin material thereto. Varying the amount of pectin present in the culture medium gel in the range of from about ten to about thirty grams of pectin per liter of medium also produces suitable gels under the prior examples. Most preferably the multivalent metal cation material comprises a calcium salt, and variation of the amount of calcium cations from about fifteen to about thirty milligrams of cations per gram of pectin provides a suitable gel in accordance with the prior examples. Although the most preferred ranges for amount of pectin and amount of multivalent metal cation materials have been recited herein, suitable gels may be provided outside of these ranges and applicant does not intend to be limited to these ranges which form the most preferred embodiments of the invention.

What is claimed is:

1. A method for preparing a gelled biological growth medium which comprises the steps of:
    a. providing a predetermined amount of a liquid growth medium;
    b. providing a predetermined amount of a low methoxyl pectin material;
    c. providing a culture-growth container having a growth capatible gel therein, the growth-compatible gel containing a multivalent metal cation material suitable to produce gelling of the low methoxyl pectin material, said growth-compatible gel containing a multivalent metal cation material comprising a layer in contact with the bottom of said culture-growth container; and
    d. adding the liquid growth medium and low methoxyl pectin material to the culture growth container to produce a gelled growth medium having the low methoxyl pectin material as essentially the sole functional gelling agent.

2. The method of claim 1 in which the low methoxyl pectin material is the sole functional gelling agent.

3. The method of claim 1 in which steps a. and b. comprise providing a mixture of predetermined amounts of a liquid growth medium and a low methoxyl pectin material.

4. The method of claim 3 in which the low methoxyl pectin material has approximately a five percent methoxyl content.

5. The method of claim 3 in which the liquid growth medium includes between about ten and about thirty grams of pectin per liter of growth medium.

6. The method of claim 5 in which the multivalent metal cation material comprises calcium cations.

7. The method of claim 1 in which the growth-compatible gel comprises an agar gel.

8. The method of claim 7 in which steps a. and b. comprise providing a mixture of predetermined amounts of a liquid growth medium and a low methoxyl pectin material.

9. The method of claim 8 in which the low methoxyl pectin material has approximately a five percent methoxyl content.

10. The method of claim 9 in which the liquid growth medium includes between about ten and about thirty grams of pectin per liter of growth medium.

11. The method of claim 1 in which the combined volume of the liquid growth medium and low methoxyl pectin material is from about three to about twenty times the volume of the growth-compatible gel.

12. The method of claim 11 in which the culture-growth container is a Petri dish having a growth-compatible gel present as a film layer therein.

13. A method for preparing a gelled biological growth medium which comprises the steps of:
    a. providing a predetermined amount of a liquid growth medium;
    b. providing a predetermined amount of a low methoxyl pectin material;
    c. providing a culture-growth container having located thereon a multivalent metal cation material suitable to produce gelling of the low methoxyl material, the metal cation material forming a generally evenly distributed film layer upon a surface of the culture-growth container, said film layer of multivalent metal cation material being in contact with the bottom of said culture-growth container; and
    d. adding the liquid growth medium and low methoxyl pectin material to the culture growth container to produce a gelled growth medium having the low methoxyl pectin material as essentially the sole functional gelling agent.

14. The method of claim 13 in which step (c) comprises applying a solution of the multivalent metal cation material upon the surface of the culture-growth container and permitting the solution to dry.

15. The method of claim 14 in which the solution of multivalent metal cation material is an aqueous solution.

16. The combination useful as a biological growth medium which comprises:
    a culture growth container;
    a growth-compatible gel forming a first layer in said container, said growth-compatible gel including a material other than a pectin material as the substantial functional gelling agent and a metal cation material suitable to produce gelling of a low methoxyl pectin material, said first layer of growth-compatible gel being in contact with the bottom of said culture-growth container; and
    a growth-medium gel forming a second layer adjacent said growth-compatible gel in said container, said growth-medium gel including a growth medium and as essentially the sole functional gelling agent a low methoxyl pectin material.

17. The combination of claim 16 in which the low methoxyl pectin material is the sole functional gelling agent.

18. The combination of claim 16 in which the low methoxyl pectin material is present in an amount of from about ten to about thirty grams of pectin per liter of growth-medium.

19. The combination of claim 16 and which includes at least one buffer selected from the group consisting of $Na_2HPO_4$, $NaH_2PO_4$, $Na_3PO_4$, $NaHCO_3$ and $Na_2CO_3$.

20. The combination of claim 16 in which the low methoxyl pectin material has approximately a five percent methoxyl content.

21. The combination of claim 20 in which the multivalent metal cation material comprises calcium cations.

22. The combination of claim 21 in which the calcium cations are present in an amount of from about 15 to about 30 milligrams of calcium cations per gram of pectin.

23. The combination of claim 22 in which the low methoxyl pectin material is present in an amount of from about ten to about thirty grams of pectin per liter of medium.

24. The combination of claim 1 in which the growth-compatible gel comprises an agar gel.

25. The combination of claim 24 in which the low methoxyl pectin material has approximately a five percent methoxyl content.

26. The combination of claim 25 in which the low methoxyl pectin material is present in an amount of from about ten to about thirty grams of pectin per liter of growth-medium gel.

27. The combination of claim 26 in which the multivalent metal cation material comprises calcium cations.

28. The combination of claim 27 in which the calcium cations are present in an amount of from about 15 to about 30 milligrams of calcium cations per gram of pectin.

29. The combination of claim 16 in which the volume of the growth-medium gel is from about three to about twenty times the volume of the growth-compatible gel.

30. The combination of claim 29 having about ten milliliters of growth-medium gel and about one milliliter of growth-compatible gel.

31. The combination useful in preparing a gelled biological growth medium comprising:
a culture-growth container; and
a growth-compatible gel located in said container said growth-compatible gel including a meterial other than a pectin material as the substantial functional gelling agent, said growth-compatible gel further including a multivalent metal cation material in an amount of at least about 4 grams/100 milliliters, said growth-compatible gel containing a multivalent metal cation material comprising a layer in contact with the bottom of said culture-growth container.

32. The combination of claim 31 in which the growth-compatible gel consists essentially of the multivalent metal cation material, agar and water.

33. The combination useful in preparing a gelled biological growth medium comprising:
a culture-growth container; and
a multivalent metal cation material forming a thin, evenly distributed film upon a surface of the culture-growth container, said film of multivalent metal cation material being in contact with the bottom of said culture-growth container.

34. The combination of claim 33 in which the culture-growth container is a Petri dish having a base including an interior bottom surface, the multivalent metal cation material forming a thin film upon the interior bottom surface.

* * * * *